(12) United States Patent
Cox et al.

(10) Patent No.: US 7,688,427 B2
(45) Date of Patent: Mar. 30, 2010

(54) PARTICLE PARAMETER DETERMINATION SYSTEM

(75) Inventors: James A. Cox, New Brighton, MN (US); Christopher J. Zins, Coon Rapids, MN (US)

(73) Assignee: Honeywell International Inc., Morristown, NJ (US)

( * ) Notice: Subject to any disclaimer, the term of this patent is extended or adjusted under 35 U.S.C. 154(b) by 364 days.

(21) Appl. No.: 11/380,878

(22) Filed: Apr. 28, 2006

(65) Prior Publication Data

US 2006/0244964 A1 Nov. 2, 2006

Related U.S. Application Data

(60) Provisional application No. 60/676,403, filed on Apr. 29, 2005.

(51) Int. Cl.
*G01N 33/48* (2006.01)
(52) U.S. Cl. ...................................................... 356/39
(58) Field of Classification Search .................. 356/39, 356/73, 243
See application file for complete search history.

(56) References Cited

U.S. PATENT DOCUMENTS

| | | | |
|---|---|---|---|
| 3,390,605 A * | 7/1968 | Nagamura | ............... 356/73 |
| 3,657,537 A | 4/1972 | Wheeless, Jr. et al. | |
| 3,822,095 A | 7/1974 | Hirschfeld | |
| 3,928,094 A | 12/1975 | Angell | |
| 3,976,862 A | 8/1976 | Curbelo | |
| 4,284,412 A | 8/1981 | Hansen et al. | |
| 4,293,221 A | 10/1981 | Kay et al. | |
| 4,350,892 A | 9/1982 | Kay et al. | |
| 4,412,004 A | 10/1983 | Ornstein et al. | |
| 4,478,076 A | 10/1984 | Bohrer | |
| 4,478,077 A | 10/1984 | Bohrer et al. | |
| 4,501,144 A | 2/1985 | Higashi et al. | |
| 4,577,964 A * | 3/1986 | Hansen, Jr. | ............... 356/39 |
| 4,599,000 A | 7/1986 | Yamada | |
| 4,651,564 A | 3/1987 | Johnson et al. | |
| 4,683,159 A | 7/1987 | Bohrer et al. | |
| 4,695,034 A | 9/1987 | Shimizu et al. | |

(Continued)

FOREIGN PATENT DOCUMENTS

DE 10122321 4/2002

(Continued)

OTHER PUBLICATIONS http://www.micronics.net/tsensor.htm, 2 pages, downloaded Jun. 14, 2000.

(Continued)

*Primary Examiner*—Tarifur R. Chowdhury
*Assistant Examiner*—Isiaka O Akanbi
(74) *Attorney, Agent, or Firm*—Kris T. Fredrick

(57) ABSTRACT

A system for determining particle parameters. The system may, for example, may optically determine parameters common to a hematology analysis. Such parameters may include a red blood cell count, a platelet count, a mean cell volume and a red cell distribution width. A hematocrit parameter may be calculated. Also, a measurement of hemoglobin in a blood sample may be obtained leading to a calculation of a mean mass of hemoglobin in a red blood cell and a mean cell hemoglobin concentration. The system may be implemented in a portable cartridge type cytometer.

18 Claims, 14 Drawing Sheets

U.S. PATENT DOCUMENTS

| | | | |
|---|---|---|---|
| 4,704,033 A | 11/1987 | Fay et al. | |
| 4,745,279 A | 5/1988 | Karkar et al. | |
| 4,818,263 A | 4/1989 | Mitch | |
| 4,874,949 A | 10/1989 | Harris et al. | |
| 4,911,616 A | 3/1990 | Laumann, Jr. | |
| 4,932,989 A | 6/1990 | Presby | |
| 5,017,497 A | 5/1991 | Gerard de Grooth et al. | |
| 5,050,429 A | 9/1991 | Nishimoto et al. | |
| 5,078,581 A | 1/1992 | Blum et al. | |
| 5,082,242 A | 1/1992 | Bonne et al. | |
| 5,085,562 A | 2/1992 | van Lintel | |
| 5,096,388 A | 3/1992 | Weinberg | |
| 5,108,623 A | 4/1992 | Cangelosi et al. | |
| 5,129,794 A | 7/1992 | Beatty | |
| 5,159,642 A * | 10/1992 | Kosaka | 382/134 |
| 5,171,132 A | 12/1992 | Miyazaki et al. | |
| 5,176,358 A | 1/1993 | Bonne et al. | |
| 5,185,641 A | 2/1993 | Igushi et al. | |
| 5,194,909 A | 3/1993 | Tycko | |
| 5,219,278 A | 6/1993 | van Lintel | |
| 5,224,843 A | 7/1993 | van Lintel | |
| 5,244,537 A | 9/1993 | Ohnstein | |
| 5,323,999 A | 6/1994 | Bonne et al. | |
| 5,441,597 A | 8/1995 | Bonne et al. | |
| 5,452,878 A | 9/1995 | Gravesen et al. | |
| 5,457,526 A | 10/1995 | Kosaka | |
| 5,510,267 A | 4/1996 | Marshall | |
| 5,528,045 A | 6/1996 | Hoffman et al. | |
| 5,540,494 A * | 7/1996 | Purvis et al. | 356/73 |
| 5,570,193 A | 10/1996 | Landa et al. | |
| 5,594,544 A * | 1/1997 | Horiuchi et al. | 356/73 |
| 5,601,080 A | 2/1997 | Oppenheimer | |
| 5,616,501 A | 4/1997 | Rodriguez et al. | |
| 5,633,724 A | 5/1997 | King et al. | |
| 5,683,159 A | 11/1997 | Johnson | |
| 5,716,852 A | 2/1998 | Yager et al. | |
| 5,717,631 A | 2/1998 | Carley et al. | |
| 5,726,751 A | 3/1998 | Altendorf et al. | |
| 5,757,476 A | 5/1998 | Nakamoto et al. | |
| 5,760,900 A | 6/1998 | Ito et al. | |
| 5,793,485 A | 8/1998 | Gourley | |
| 5,799,030 A | 8/1998 | Brenner | |
| 5,822,170 A | 10/1998 | Cabuz et al. | |
| 5,836,750 A | 11/1998 | Cabuz | |
| 5,839,807 A | 11/1998 | Perlo | |
| 5,863,502 A | 1/1999 | Southgate et al. | |
| 5,880,474 A | 3/1999 | Norton et al. | |
| 5,893,722 A | 4/1999 | Hibbs-Brenner et al. | |
| 5,901,939 A | 5/1999 | Cabuz et al. | |
| 5,922,210 A | 7/1999 | Brody et al. | |
| 5,932,100 A | 8/1999 | Yager et al. | |
| 5,948,684 A | 9/1999 | Weigl et al. | |
| 5,970,315 A | 10/1999 | Carley et al. | |
| 5,971,158 A | 10/1999 | Yager et al. | |
| 5,972,710 A | 10/1999 | Weigl et al. | |
| 5,974,867 A | 11/1999 | Forster et al. | |
| 6,007,775 A | 12/1999 | Yager | |
| 6,032,689 A | 3/2000 | Tsai et al. | |
| 6,054,335 A | 4/2000 | Sun et al. | |
| 6,082,185 A | 7/2000 | Saaski | |
| 6,091,197 A | 7/2000 | Sun et al. | |
| 6,091,537 A | 7/2000 | Sun et al. | |
| 6,094,293 A | 7/2000 | Yokoyama et al. | |
| 6,097,485 A | 8/2000 | Lievan | |
| 6,097,859 A | 8/2000 | Solgaard et al. | |
| 6,106,245 A | 8/2000 | Cabuz | |
| 6,109,889 A | 8/2000 | Zengerle et al. | |
| 6,116,756 A | 9/2000 | Peeters et al. | |
| 6,124,663 A | 9/2000 | Haake et al. | |
| 6,139,800 A | 10/2000 | Chandler | |
| 6,179,586 B1 | 1/2001 | Herb et al. | |
| 6,184,607 B1 | 2/2001 | Cabuz et al. | |
| 6,215,221 B1 | 4/2001 | Cabuz et al. | |
| 6,237,619 B1 | 5/2001 | Maillefer et al. | |
| 6,240,944 B1 | 6/2001 | Ohnstein et al. | |
| 6,249,341 B1 | 6/2001 | Basiji et al. | |
| 6,281,975 B1 | 8/2001 | Munk | |
| 6,317,511 B1 * | 11/2001 | Horiuchi | 382/133 |
| 6,382,228 B1 | 5/2002 | Cabuz et al. | |
| 6,549,275 B1 | 4/2003 | Cabuz et al. | |
| 6,597,438 B1 | 7/2003 | Cabuz et al. | |
| 2003/0142291 A1 | 7/2003 | Padmanabhan et al. | |
| 2004/0223135 A1 | 11/2004 | Ortyn et al. | |
| 2005/0255600 A1 * | 11/2005 | Padmanabhan et al. | 436/63 |
| 2006/0119836 A1 * | 6/2006 | Ku | 356/39 |
| 2007/0190525 A1 * | 8/2007 | Gu et al. | 435/5 |

FOREIGN PATENT DOCUMENTS

| | | |
|---|---|---|
| EP | 0269076 | 6/1988 |
| EP | 1001326 | 5/2000 |
| EP | 1134548 | 9/2001 |
| JP | 61066947 | 4/1986 |
| JP | 10073528 | 3/1998 |
| JP | 2000056228 | 2/2000 |
| WO | 9527199 | 10/1995 |
| WO | 9960397 | 11/1999 |
| WO | 0109598 | 2/2001 |
| WO | 0210713 | 2/2002 |
| WO | 0210714 | 2/2002 |
| WO | 2005114142 | 12/2005 |

OTHER PUBLICATIONS http://www.micronics.net/hfilter.htm, pp. 1-3, downloaded Jun. 14, 2000.

http://www.micronics.net/mcytometry.htm, pp. 1-4, downloaded Jun. 14, 2000.

http://www.micronics.net/orcafluidics.htm, pp. 1-4, downloaded Jun. 14, 2000.

Altendorf et al, "Results Obtained Using A Prototype Miorofluidios-Based Hematology Analyzer", SPIE Biomedical Optics 97, 1997.

Altendorf et al., "Differential Blood Cell Counts Obtained Using A Microchannel Based Flow Cytometer," Solid State Sensors & Actuators, vol. 1, 531, 1997.

Altendorf et al., "Implementation Of Novel Optical Detection Methods For Clinically Important Blood Analytes Using Microfabricated Flow Structures (T-Sensors™)," MicroTAS 98, Banff, Canada, Apr. 1998.

Altendorf et al., "Microfabrication Technology For Research And Diagnostics, Silicon Microchannel Optical Flow Cytometry," SPIE Proceedings, Biomedical Optics 96, Jan. 1996.

Cabuz et al., "Mesoscopic Sampler Based on 3D Array of Electrostatically Activated Diaphragms", The 10th Int. Conf. On Solid-State Sensors and Actuators, Transducers'99, Sendai Japan, p. 1890-1 Jun. 7-12, 1999.

Darling et al., "Integration Of Microelectrodes With Etched Microchannels For In-Stream Electrochemical Analysis", MicroTAS 98, Banff, Canada, Apr. 1998.

Dunn et al., "Three-Dimensional Computation of Light Scattering from Cells," IEEE Journal of Selected Topics in Quantum Electronics, vol. 2, No. 4, pp. 898-905, Dec. 1996.

Fedder et al., "Laminated High-Aspect-Ratio Microstructures in a Conventional CMOS Process", Proc. Micro Electro Mechanical Systems Workshop, MEMS 96, San Diego, California, Feb. 11-15, 1996, pp. 13-18.

Hammer et al., "Single Scattering by Red Blood Cells," Applied Optics, vol, 37, No. 31, pp. 7410-7418, Nov. 1, 1998.

Hatch et al., "Microfluidic Approaches To Immunoassays", SPIE conference on Micromachining and Microfabrication Symposium at Santa Clara, CA, Sep. 20-22, 1999.

Huang et al., "Development Of A Flow Cytometry Based Miniature Chemical Fluid Analysis System Using Fluorescent Microbeads", SPIE Biomedical Optics, BIOS 97, conference proceedings, 1997.

Kleinfeld et al., "Detection of Action Potentials in Vitro by Changes in Refractive Index," Light Scattering Imaging of Neural Tissue Function: The Humana Press Inc., 8 pages, 2003.

Lehman et al., "High-Frequency Modulation Characteristics of Red VCSELs", Electronics Letters, Feb. 13, 1997, vol. 33(4), pp. 298-300. Copyright 1997 IEE.

Maltsev et al., "Absolute Real-Time Measurement of Particle Size Distribution with the Flying Light-Scattering Indicatrix Method," Applied Optics, vol. 35, No. 18, pp. 3275-3280, Jun. 20, 1996.

Maltsev et al., "Parametric Solution of the Inverse Light-Scattering Problem for Individual Spherical Particles," Applied Optics, vol. 36, No. 24, pp. 6102-6108, Aug. 20, 1997.

Maltsev, "Scanning Flow Cytometry for Individual Particle Analysis," Review of Scientific Instruments, vol. 71, No. 1, pp. 243-255, Jan. 2000.

Ohnstein et al., "Micromachined Silicon Microvalve", Proceedings of MEMS, 1990, IEEE Micro Electromechanical Systems, Napa Valley, California, Feb. 11-14, 1990, pp. 95-98.

Roulet et al., "Fabrication of Multilayer Systems Combining Microfluidic and Microoptical Elements for Fluorescence Detection," Journal of Microelectromechanical Systems, vol. 10, No. 44, pp. 483-491, Dec. 4, 2001.

Sernyanov et al., "Calibration-Free Method to Determine the Size and Hemoglobin Concentration of Individual Red Blood Cells from Light Scattering," Applied Optics, vol. 39, No. 31, pp. 5884-5889, Nov. 1, 2000.

Shapiro, "Practical Flow Cytometry", third edition, p. 237, 1995.

Shvalov et al., "Light-Scattering Properties of Individual Erythrocytes," Applied Optics, vol. 38, No. 1, pp. 230-235, Jan. 1, 1999.

Strzelecka et al., "Parallel Free-Space Optical Interconnect Based on Arrays of Vertical-Cavity Lasers and Detectors with Monolithic Microlenses", Applied Optics, vol. 37, No. 14, pp. 2811-2821, May 10, 1998.

Terstappen et al., "Four-Parameter White Blood Cell Differential Counting Based on Light Scattering Measurements", Alan R. Liss, Inc., Cytometery 9:39-43, 1988.

Toshiyoshi et al., "Micromechanical Lens Scanner for Fiber Optic Switches", Proc. 3rd International Conference on Micro Opto Electro Mechanical Systems (MOEMS 99), pp. 165-170, Aug. 30-Sep. 1, 1999.

Toshiyoshi et al., "Surface micromachined 2D Lens Scanner Array", Proc. IEEE?LEOS International Coference on Optical EMMS/ Sheraton Kauai Resort, Kauai, Hawaii, Aug. 21-24, 2000, 3 pages.

Tuantranont et al., "Flip Chip Integration of Lenslet Arrays on Segmented Deformable Micromirrors", Part of the Symposium on Design, Test and Microfabrication of MEMS and MOEMS, Paris, France, SPIE vol. 3680, 0277-786X/99, pp. 668-678, Mar.-Apr. 1999.

Tuantranont et al., "MEMS-Controllable Microlens Array For Beam Steering and Precision Alignment in Optical Interconnect Systems", Solid-State Sensor and Actuator Workshop, Hilton Head Island, South Carolina, pp. 101-104. Jun. 4-8, 2000.

Tycko et al., "Flow-Cytometric Light Scattering Measurement of Red Blood Cell Volume and Hemoglobin Concentration," Applied Optics, vol. 24, No. 9, pp. 1355-1365, May 1, 1985.

Weigl et al, "Silicon-Microfabricated Diffusion-Based Optical Chemical Sensor", Reprint from "Sensors & Actuators" B 38-39, 452-457, 9 pages, 1997.

Weigl et al, "Microfluidic Diffusion-Based Separation And Detection", Science, vol. 283, pp. 346-347, Jan. 15, 1999.

Weigl et al, "Optical And Electrochemical Diffusion-Based Detection Of Analytes In Complex Samples Using Microfabricated Flow Structures (T-SensorSTM)", Micro- and Nanofabricated Electro Optical Mechanical Systems for Biomedical and Environmental Applications II- SPIE vol. 3606, Jun. 1999.

Weigl et al, "Simultaneous Self-Referencing Analyte Determination In Complex Sample Solutions Using Microfabricated Flow Structures (T-Sensors™)", Proceedings of MicroTAS 98, 81-4, Banff, Canada, 1998.

Weigl et al., "Diffusion-Based Optical Chemical Detection In Silicon Flow Structures", B. Weigl et al., Analytical Methods & Instrumentation, µTTAS 96 special edition, 21 pages, 1996.

Weigl et al., "Fluorescence And Absorbance Analyte Sensing in Whole Blood And Plasma Based On Diffusion Separation In Silicon-Microfabricated Flow Structures," Biomedical Optics, vol. 6, No. 1, 11 pages, Jul. 1997.

Weigl et al., "Rapid Sequential Chemical Analysis Using Multiple Fluorescent Reporter Beads", Analytical Methods and Instruments, Special Issue µTTAS 96, p. 255, 1996.

Weigl, "Microfluidic Diffusion Based Electrochemical Detection Using Microfabricated Flow Structures (T-Sensors™)", Analytical Chemistry, submitted 1999.

Weigl, "Whole Blood Assays Using Microfluidics-Based T-Sensor Technology", Medical Design Online, http://news.medicaldesignonline.com/featuresarticles/19990416-5922.html, 4 pages, Apr. 16, 1999.

Yager et al., "Applying Microfluidic Chemical Analytical Systems To Imperfect Samples", Micro Total Analysis Systems 98, Kluwer Academic Publishers, Dordrecht, pp. 207-212, 1998.

Yager et al., "Design Of Microfluidic Sample Preconditioning Systems For Detection of Biological Agents In Environmental Samples", SPIE Proceedings, 3515, 252-259, 1998.

* cited by examiner

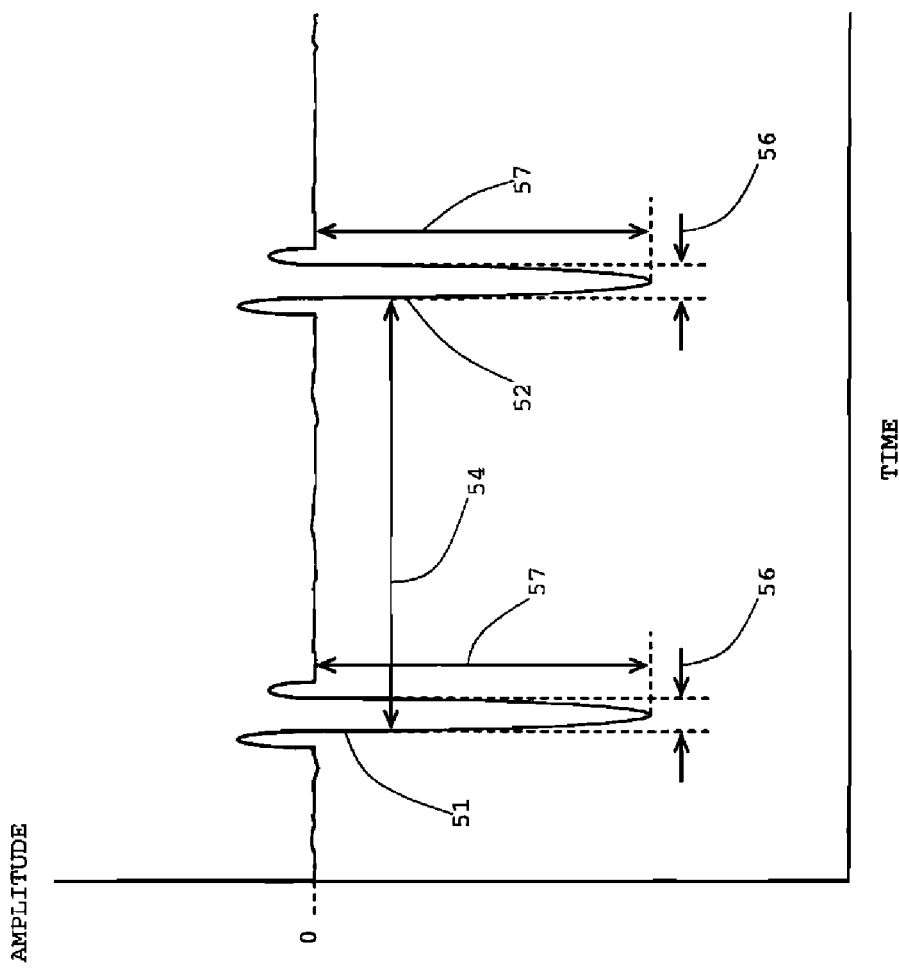
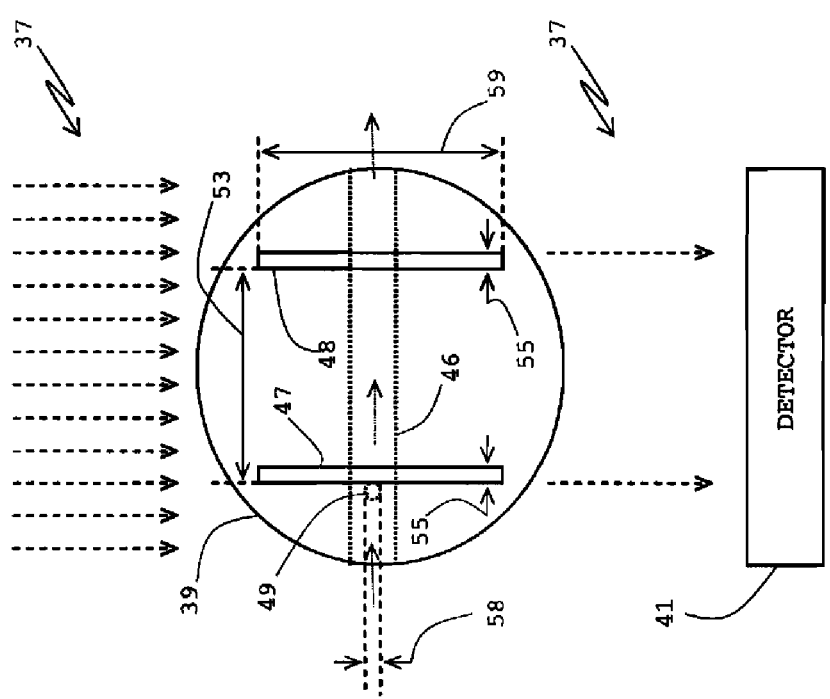

SCATTERING PARAMETERS FOR VARIOUS CELL TYPES

| CELL TYPE | CELL DIAMETER ($\mu m$) | CELL AREA ($\mu m^2$) | Cext-Csca (0.28) ($\mu m^2$) |
|---|---|---|---|
| PLT | 1.0 | 0.785 | 0.023 |
| PLT | 2.0 | 3.142 | 0.051 |
| RBC | 4.5 | 15.904 | 1.547 |
| RBC | 5.0 | 19.635 | 1.961 |
| PS BEAD | 5.43 | 23.157 | 14.585 |
| RBC | 5.5 | 23.758 | 2.209 |
| RBC | 6.0 | 28.274 | 2.880 |

FIGURE 5

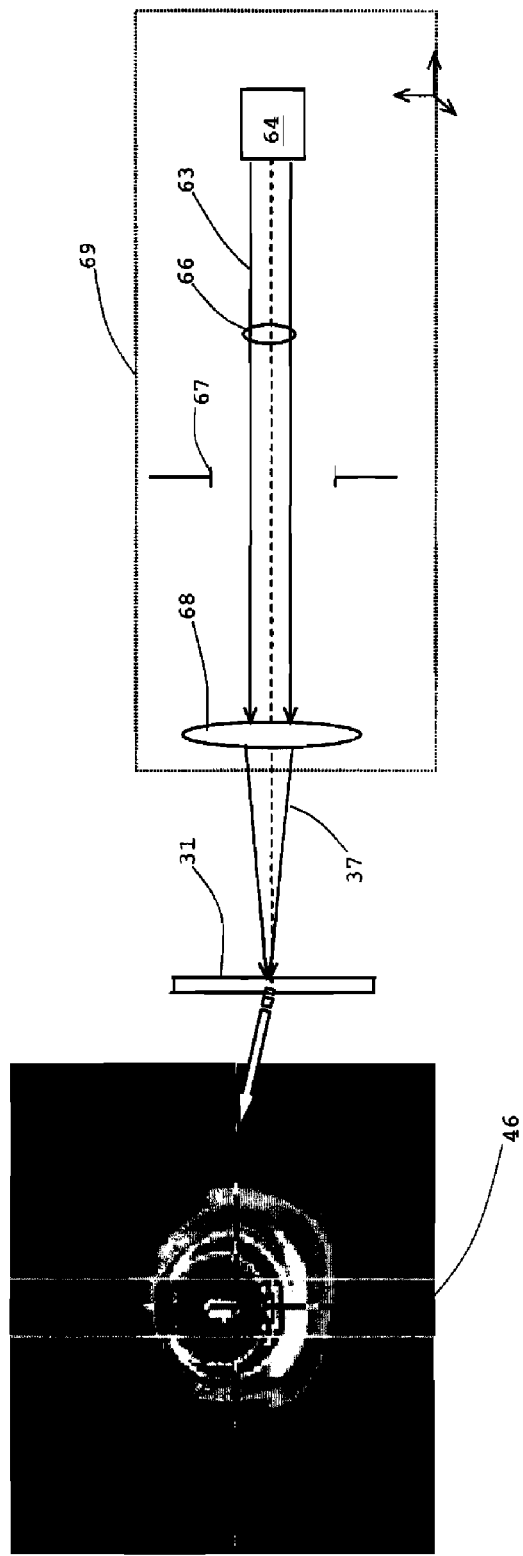
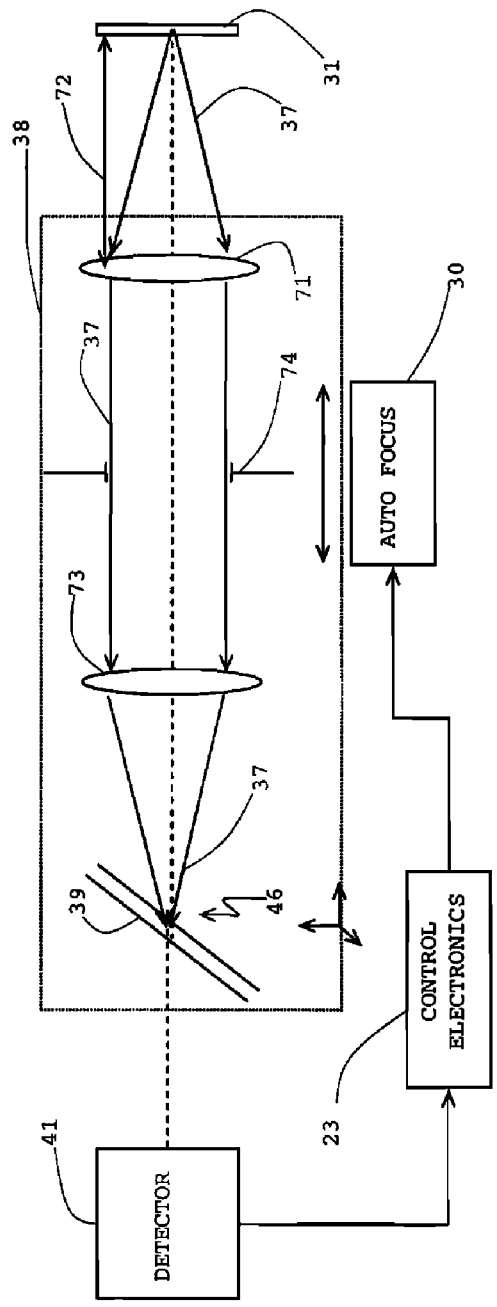
FIGURE 6a
FIGURE 6b

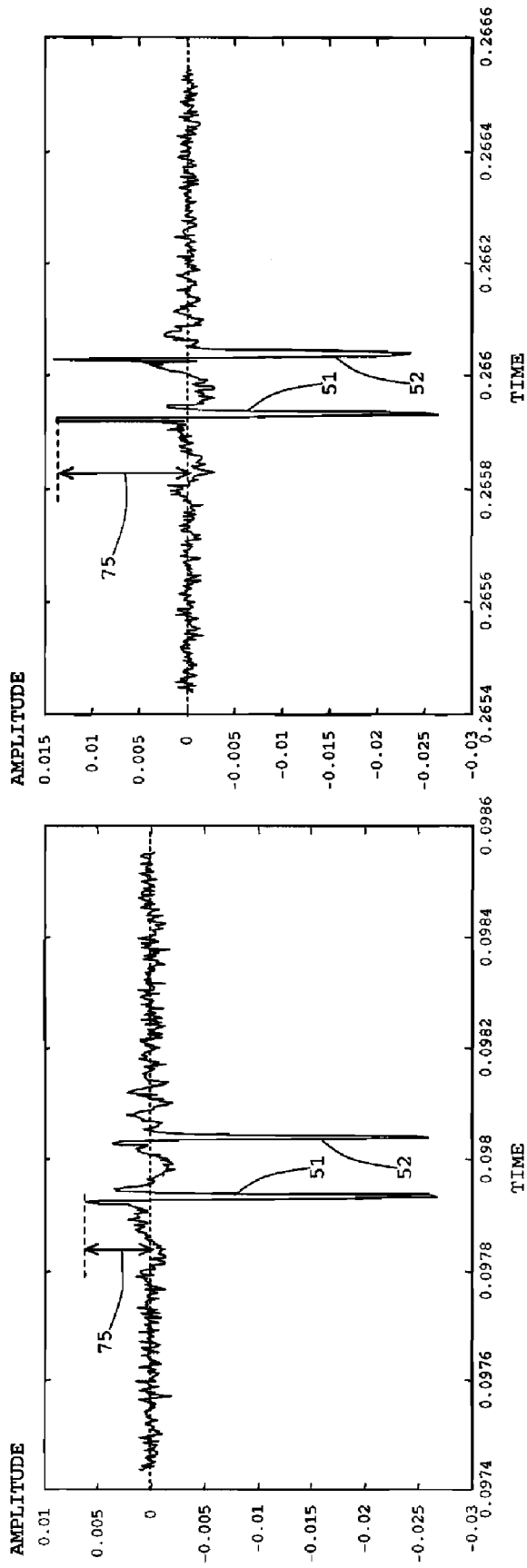

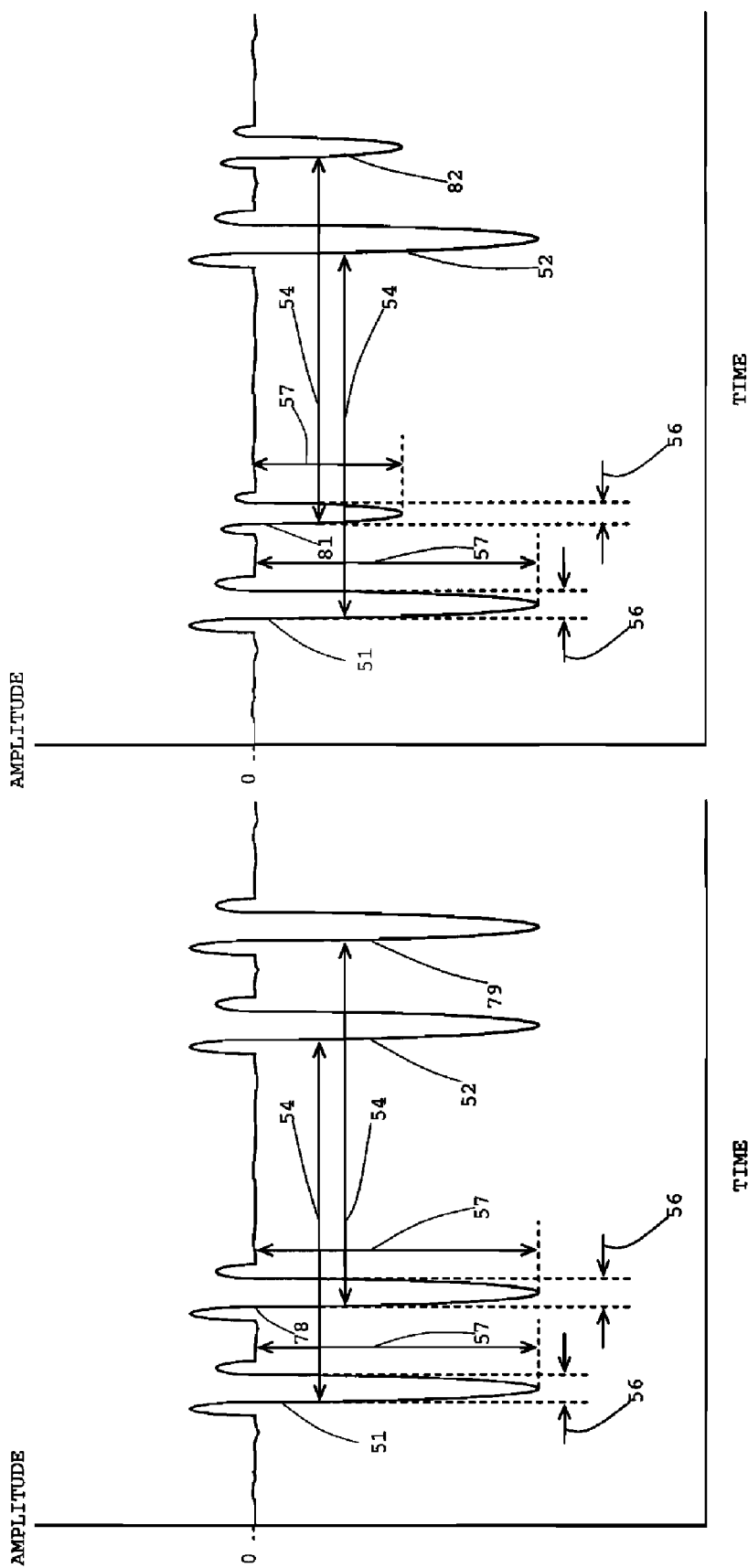

US 7,688,427 B2

PARTICLE PARAMETER DETERMINATION SYSTEM

BACKGROUND

The present invention claims the benefit of U.S. Provisional Patent Application No. 60/676,403, filed Apr. 29, 2005. U.S. Provisional Patent Application No. 60/676,403, filed Apr. 29, 2005, is hereby incorporated by reference.

The invention pertains to determining characteristics of particles. Particularly, the invention pertains to determining the count and size of particles, and more particularly, it pertains to determining such characteristics of cells.

Patents and applications related to the present invention may include: U.S. Pat. No. 6,597,438, issued Jul. 22, 2003, and entitled "Portable Flow Cytometry"; U.S. Pat. No. 6,970,245, issued Nov. 29, 2005, and entitled "Optical Alignment Detection System; U.S. Pat. No. 5,836,750, issued Nov. 17, 1998, and entitled "Electrostatically Actuated Mesopump Having a Plurality of Elementary Cells"; U.S. patent application Ser. No. 11/027,134, filed Dec. 30, 2004, and entitled "Optical Detection System with Polarizing Beamsplitter; U.S. patent application Ser. No. 10/908,543, filed May 16, 2005, and entitled "Cytometer Analysis Cartridge Optical Configuration"; and U.S. patent application Ser. No. 10/908,014, filed Apr. 25, 2005, and entitled "A Flow Control System of a Cartridge"; all of which are hereby incorporated by reference.

SUMMARY

The invention may be a system for counting, discriminating and measuring particles, such as blood cells.

BRIEF DESCRIPTION OF THE DRAWING

FIG. 3a is a view of a dual slit aperture with an image of the flow channel and a particle subject to analysis;

FIG. 3b reveals a waveform of a signal from a dual slit detector of a particle as its image crosses the slits;

FIG. 5 is a table of parameters for various particle types;

FIG. 6a is a diagram of source portion of a counting and measurement system;

FIG. 6b is a diagram of a collection optics module for beam conditioning;

FIGS. 7a and 7b show waveforms from a dual slit detector revealing a focused and a defocused image of a flow channel with a particle crossing a dual slit aperture;

FIG. 9a is a detector waveform of a complex waveform of particles of about the same size;

FIG. 9b is a detector waveform of a complex waveform of particles of different sizes;

DESCRIPTION

The present invention may be used to count and discriminate cells (e.g., RBCs, PLTs, and the like) and measure cell size (diameter, volume) in a cytometer channel using optical sensing. A laser (or other) source may be focused into a cytometer or flow channel, either as an elongated line source or as two separate spot sources. The cells may be made to flow in the cytometer channel through the focused light. High quality collection optics may be used to form a sharp image of the cells and focus illumination onto a mask, plate or an opaque screen containing one, two or more parallel slits whose longitudinal axes are preferably arranged orthogonal to the flow direction in the cytometer channel. The distance between the slits may be, for example, on the order of the mean cell separation expected in the cytometer channel. The opaque screen containing the slits may be placed in front of one or more detectors. As the image of a cell passes over a slit, it may partially obscure the light incident on the slit and cause a reduction in the signal on the detector, producing a pulse waveform whose width is proportional to the cell diameter. When two spaced slits are provided, the two waveforms may permit the calculation of the cell flow velocity, and the cell size. High signal-to-noise may be obtained, and this would permit the easy counting of events and identification of multiple cell events. Pulse width and amplitude may further enable the discrimination of cell types.

In some cases, an image of both the cell and the light source may be projected on a double slit aperture placed in front of a detector. The double slit aperture may provide a well-defined geometrical aperture and high signal-to-noise ratio to count cells. Signals from the slits may permit the accurate measurement of cell flow velocity, which in turn can aid in the calculation of a cell diameter.

Figure 1:
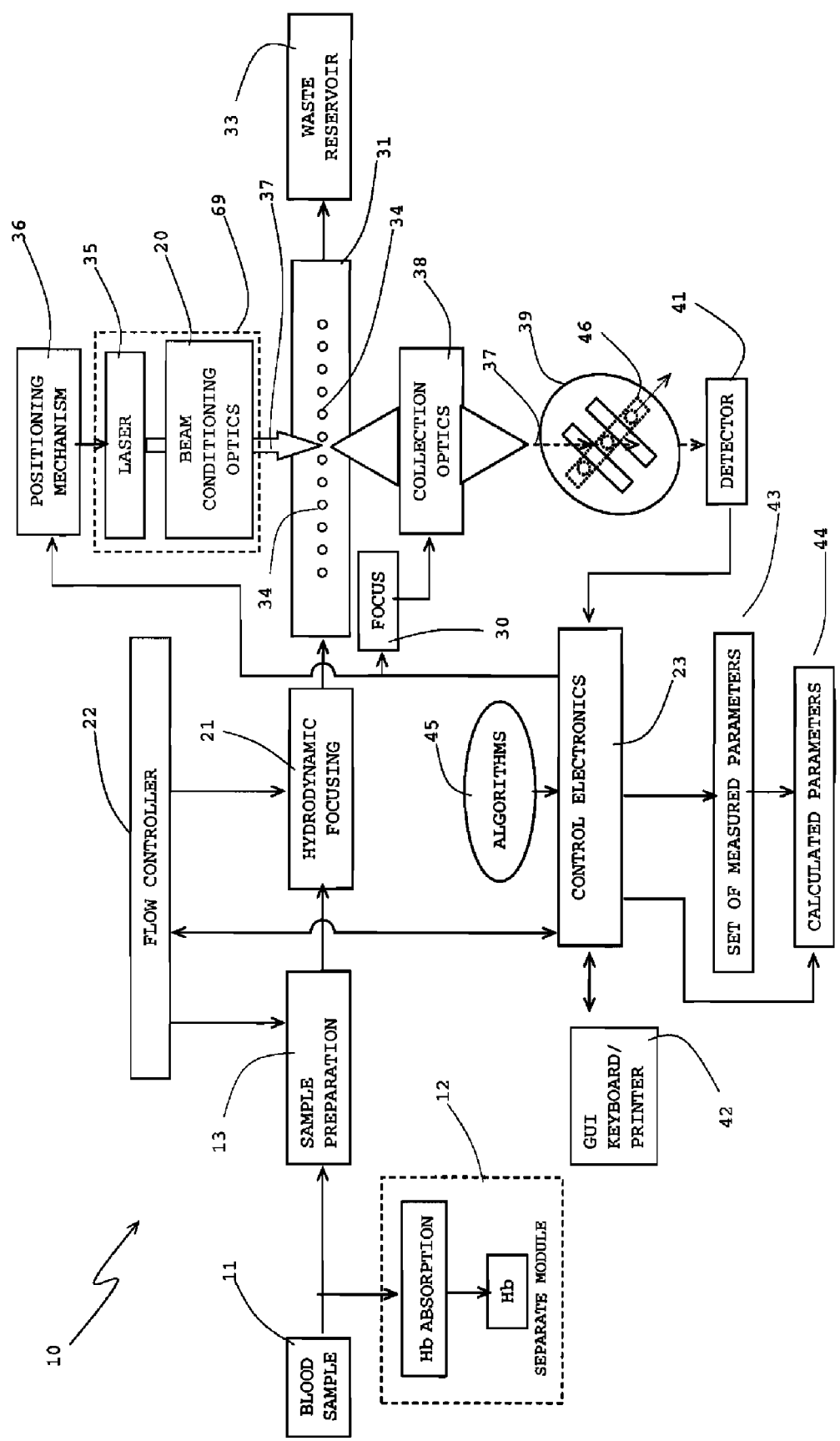
FIG. 1 is a block diagram of a particle counting and size measurement system.

FIG. 1 shows a diagram of a system 10 for attaining parameters for a hematology analysis. Four main or major parameters, a red blood cell (RBC) count (cells/µL), a platelet (PLT) count (cells/µL), a mean cell volume (MCV), and a red cell distribution width (RDW) may be attained with an optical approach upon a blood sample. MCV is effectively a measurement of the average size of the RBCs. RDW is the variation of the size among the RBCs. A greater variation of the sizes of the RBCs, the greater is the RDW.

An RBC count is an actual number of RBCs per unit volume of the blood under analysis. Hct is hematocrit which is RBC×MCV, and may amount to a measure of oxygen carrying capacity of the blood (i.e., total capacity of all of the cells in the unit volume under analysis). Hct may also be regarded as an amount of space that the RBCs take up in the blood, or the proportion of the whole blood that is composed of red blood cells. MCH is the "mean cell hemoglobin" which is effectively the amount of hemoglobin in each RBC. MCH may be regarded as the mean or approximately an average mass of hemoglobin in an individual RBC, in units of picograms. MCH=Hb÷RBC. Hb is the amount of hemoglobin per unit volume of the sample under analysis. MCHC is the "mean cell hemoglobin concentration" which may be regarded as the concentration of hemoglobin per unit volume in each of the RBCS. MCHC=Hb÷Hct.

System 10 may provide information via the control electronics 23 from essentially optical techniques including a set of measured parameters which include cell flow rate (FR), measurement time (T), dilution factor (DF), number of RBCs counted ($N_{RBC}$), number of platelets counted ($N_{PLT}$), the amount of hemoglobin (Hb), and the diameter (microns) of virtually each cell$_i$ (drbc$_i$). <drbc$_i$> is the average of the measured cell diameters of the cells, denoted by the set {drbc$_i$}. Some of the major calculated parameters may include: RBC=$N_{RBC}$÷(DF×FR×T); PLT=$N_{PLT}$÷(DF×FR×T); MCV=(π/6)×<drbc$_i^3$>; and RDW=SD{[(π/6)drbc$_i^3$]}÷MCV, where SD denotes the standard deviation of the measured quantities. Calculated parameters may include: Hct=RBC×MCV; MCHC=Hb÷Hct; and MCH=MCHC×MCV.

A blood sample 11 may be obtained for testing. A separate module 12 may be used for determining an amount of hemoglobin (Hb) or hemoglobin concentration in the blood sample. Module 12 may use hemoglobin absorption to determine the Hb. The amount of hemoglobin in the blood may be expressed in grams per liter.

The blood sample 11 may go on to a sample preparation module 13. The red blood cells may be turned from nonspheric shapes into spheres. The original shape of a red blood cell tends to be a flat cupped shape. This reshaping may be referred to as isovolumetric sphering. A sphering fluid may be used for reshaping the red blood cells into sphere-like cells, as described, for example, by Ornstein and Kim in U.S. Pat. No. 4,412,004. The sphering fluid appears to just affect the red blood cells of the sample.

Figure 2:
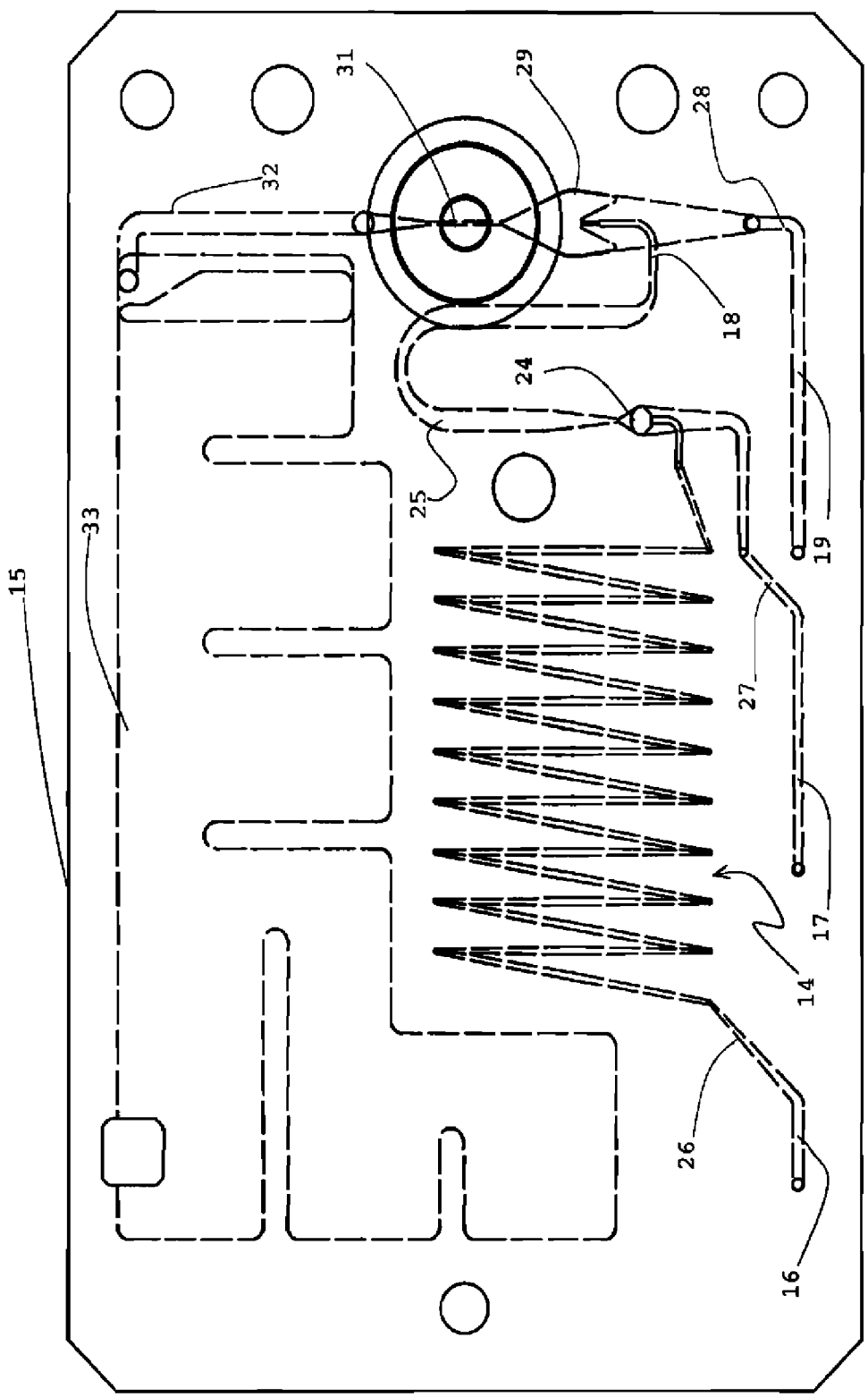
FIG. 2 shows an illustrative blood analysis cartridge.

Also, in the sample preparation may be a dilution of sample 11. Dilution is for reducing the number of red blood cells per unit volume. For example, blood has about four to five million red cells per microliter. An objective is to reduce the density of cells per unit volume and dilute the sample by an appropriate amount, for example, at a 300 to one ratio, which may reduce the number of red cells per unit volume by that ratio. Further, the number of platelets and white blood cells may be similarly reduced per unit volume. Normally, there are about 300,000 platelets pre microliter and 8,000 white blood cells per microliter. Because of the relatively low number of white blood cells, there is no need to segregate them since their effect on the counts of red blood cells and platelets is minimal. Fluid may be introduced into a sample fluid reservoir or channel 14 of a card 15 shown in FIG. 2. The disposable cartridge or card 15 is just illustrative example of part of an implementation of the invention. The invention may be implemented without the cartridge or card. Flow rates for the sample and the sphering/dilution fluid are chosen to achieve the desired dilution factor. For example, the sample may be flowing in port 16 with a rate of about one microliter per minute, and the sphering and dilution fluid may be pushed in at a rate of about 300 microliters per minute in port 17, to result in the 300 to one dilution factor where it goes to junction 24 to join the blood in the sphering channel 25. These flow rates may be sensed by flow sensors placed at the fluid supply devices. A sheathing fluid may be input to port 19 at a flow rate appropriate needed to shape the sample 11 flow to form a core with hydrodynamic focusing 21. The flow rates of the sample, the sphering and dilution fluid, and the sheathing fluid may be controlled by a flow controller 22 which receives rate signals from the control electronics 23. The result of hydrodynamic focusing 21 is that the cells form a single file in the core during its flow in the channel 31.

The sample may be pushed into channel 26, which may taper as it extends to its connection with the sample channel 14. The taper may be for bubble suppression. The sphering reagent is pushed in port 17 through channel 27 which is narrower or smaller than the pusher channel 26 for bubble suppression. The sheath channel 28 from port 19 to the focusing chamber 29 may be slightly smaller for similar reasons. The sheath fluid may flow around the sample coming out of channel 18 into chamber 29 and hydro focus the particles of the sample into a single file for a flowing through a cytometer optical channel 31. After flowing through the optical channel, the sample and other fluids may flow into the waste reservoir 33 via a channel 32.

RBCs, platelets, and WBCs 34 may flow through optical channel 31. While in the optical channel 31, particles 34 may cross a light beam 37 from a laser 35. A positioning mechanism 36 may adjust laser 35 so that it is appropriately directed to the optical channel 34. The positioning mechanism may be connected to and controlled by electronics module 23. A set of beam conditioning optics 20 may provide spot distribution and focus of light beam 37 on the channel 31. The focus of light beam 37 by collection optics module 38 may be facilitated by a focusing mechanism 30 which is connected to and receives control signals from the control electronics module 23. As light 37 passes through channel 31, it may be obscured momentarily by particles 34 passing through the channel. After light 37 passes through the optical channel 31, it may go through collection optics module 38 for image quality control. Light beam 37 may go through a double-slit opaque screen, plate or mask 39 and on to a dual slit detector 41. The detector 41 may be a dual or an ordinary single sensor light detector. It may be a multiple sensor detector for a mask having more than two slits. Output signals from, for example, the dual slit detector 41 may go to control electronics 23 for data acquisition and analysis, and report generation. Connected to control electronics 23 may be a general user interface (GUI) keyboard and printer 42. Output by the control electronics module 23 may be a set of measured parameters 43 from the duel slit detector 41 as processed by electronics module 23. Control electronics 23 may incorporate a precision clock for timing purposes such as the velocity of particles 34 in the flow channel 31, sampling data points of a pulse, and other parameters. From the parameters 43, a set of calculated parameters 44 may be provided. An algorithm module 45 may provide algorithms to control electronics module 23 for data analysis, parameter calculations and other processing activities.

Here, an emphasis of system 10 may be data or parameter acquisition and tabulation. Item 39 may be a mask or an aperture arrangement having two slot-like openings or slits 47 and 48 as shown in FIGS. 1 and 3. Item 39 could have any number of openings or slits. However, for illustrative purposes, two slits may be referred to. On the aperture arrangement may be an image 46 of the channel 31 with a core of single file particles 34. FIG. 3a, an enlargement of item 39 is shown. A particle 34 may be represented by an image 49 (or its shadow).

One particle 34, which may be a red blood cell, as represented in the image 46 (may be referred to as particle 49) in FIG. 3a, is shown for illustrative purposes. As particle 49 crosses slit 47, it may obscure light 37 of slit 47 and detector 41 may sense a decrease of light 37 and output a signal representative of that obscuration to control electronics 23. This signal may be represented by a waveform 51 in an amplitude versus time chart of FIG. 3b. Particle 49 may continue to travel through the channel image 46. After traveling a distance 53, particle 49 may cross slit 48 and obscure light 37 of slit 48 and detector may sense a decrease of light 37 and output a signal representative of that obscuration to control electronics 23. This signal may be represented by a waveform 52 as shown in FIG. 3b. A dimension 54 may represent an amount of time (transit time) between waveforms 51 and 52 which is the amount of time that it took particle 49 to travel the distance 53. Dimension 53 may be regarded as a slit pitch. Dimension 55 may be a width of the slits 47 and 48. Dimension 56 may represent the width of waveform or pulse 51 and waveform or pulse 52, which is indicated in terms of time. Dimension 57 may indicate a magnitude or amplitude of pulse 51 and pulse 52. The width and amplitude of the pulses 51 and 52 may lead to a determination of the cell diameter and type. The diameter 58 of a particle or cell 34 (i.e., particle 34 image 49) may equal a calibration constant times pulse width (in terms of distance) minus width 55. Several formulas may include: Cell diameter 58=C(pulse width (in distance)) minus slit width 55; Pulse width (in distance)=flow velocity times pulse width 56 (in time); Pulse width (in distance)=((slit pitch 53) divided by (transit time 54)) times pulse width 56 (in time).

Figure 4B:
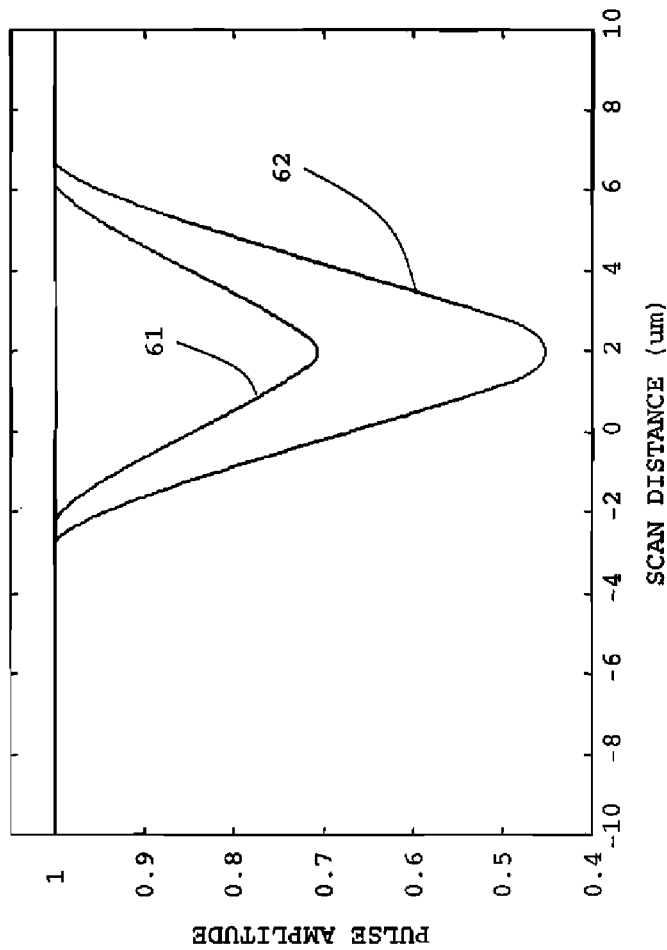
FIG. 4b is a graph of signals of two sizes of a cell as its image crosses a slit aperture.
Figure 4A:
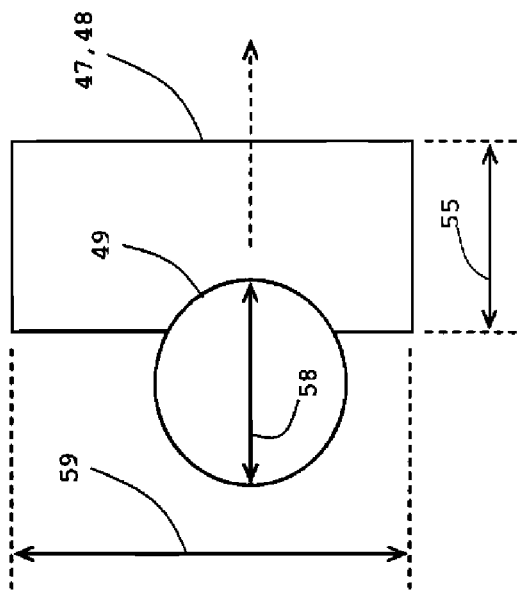
FIG. 4a shows an image of a single cell as it crosses a slit.

FIGS. 4a and 4b show a simple model of cell image 49 and of the slit detector signal graph, respectively. The cell image 49 may be one of a circular cell with a diameter dimension 58. Also shown in FIG. 4a is a rectangular slit 47 or 48 having a width dimension 55 and a length dimension 59. One may assume uniform illumination of the actual cell 34 for the image 49 of it, with no diffraction, for a simple model of a pulse waveform from a detector at the other side of the slit aperture relative to the cell and illumination. The pulse width (in distance) may equal the calibration constant times a quantity of a cell diameter 58 plus slit width 55. The calibration factor may be assumed to equal one which would be the cell image 49 at focus with no diffraction. An approximate estimate of the relative pulse amplitude 57 of various types of cells may equal $C_{ext} - C_{sca}$ (Numerical Aperture), where $C_{ext}$ is a total Mie extinction cross-section and $C_{sca}$ is a Mie scattering cross-section into optics numerical aperture (NA). The graph of FIG. 4b shows detector pulses 61 and 62 which represent red blood cells having diameters of 4.5 microns and 5.5 microns, respectively. The pulse of a platelet having a 2 micron diameter would be significantly smaller than pulse 61. FIG. 5 shows a table of the scattering parameters for various cell types, platelets (PBT), red blood cells (RBC) and beads with the cell diameter, cell cross-section area and the $C_{ext} - C_{sca}$ (NA=0.28) in micron dimensions. The $C_{ext} - C_{sca}$ may be a basis for estimating relative pulse amplitudes.

One may calculate pulse width, amplitude and calibration factor (C) using an algorithm. An applicable formula may include "Pulse width (in distance)=C(Diameter$_{cell}$ plus slit width)".

As to focus sensitivity, about a 10 micron focus change may result in about a 0.5 micron error in cell or particle diameter, that is, about a 10 percent error in diameter, or about a 30 percent error in volume. The calibration may vary significantly from cart to card; for instance, one may calculate the calibration factor (C) with 5.43 micron beads introduced at the start of the blood analysis and apply it to subsequent blood cells in the sample. Therefore, a means of determining the calibration factor in situ using, for example, precision beads, may be necessary.

FIG. 6a shows a source leg 69 of a test system. There may be a 670 nm laser 64 with a collimated beam 63. There may be an iris 67 for light control, beam conditioning optics, and a focusing optic 68 for focusing a beam 37 on a cytometer channel 31. There may be a distribution of light 37 in a cell 34. An image 46 may be projected from the cytometer channel 31 on to a double slit aperture 39 as shown in FIG. 6b, which shows an illustrative example of a collection optics module 38. Light 37 may emanate with an image 46 from channel 37 to a collimating optic 71 (e.g., Mitutoyo M Plan Apo 10, NA=0.28). Optic 71 may be a distance 72 from channel 31. Distance 72 may be about 33.5 mm in this example. Collimated light 37 may propagate from optic 71 to a focusing optic 73 (e.g., Mitutoyo M Plan Apo 10, NA=0.28). Optic 73 may focus light 37 containing the image 46 onto the double slit aperture 39. There may be an iris 74 for controlling an amount of light through the collection optics 38.

There may be a focus or auto focus module 30. The auto focus may involve a closed-loop control that determines, according to the waveform 51, 52 signal from the detector 41, how much to move the position of optic 73 relative to optic 71 and/or aperture 39. In some configurations, optic 71 may also be movable for focus 30.

FIGS. 7a and 7b show pictures of waveforms 51 and 52 which reveal a feature of a focused or unfocused image 46 on aperture 39. These waveforms resemble actual detector 41 output waveforms possibly with some noise introduced into detector 41. A criterion upon which control electronics 23 may rely on for determining the focus of image 46 is a highest amplitude 75 of the waveform 51, 52 above the zero amplitude. This amplitude or distance 75 of up-shoots should be kept at a minimum for a favorable focus. FIG. 7a is an illustrative example of the waveform 52, 53, where the image 46 is in focus. FIG. 7b is an illustrative example of the waveform 53, 53, where the image 46 is defocused. Control electronics 23 in conjunction with detection 41 and focus module 30 may result in an adjustment or movement of the position of lens 73 and/or 74 so that the amplitude 75 of the waveform 51, 52 is at a minimum. The need to focus the image on the slit aperture is because such focus may vary from cartridge to cartridge. The focusing may be done with precision beads. After that, the calibration factor may be calculated with the knowledge of the diameter of the precision test beads.

Figure 8B:
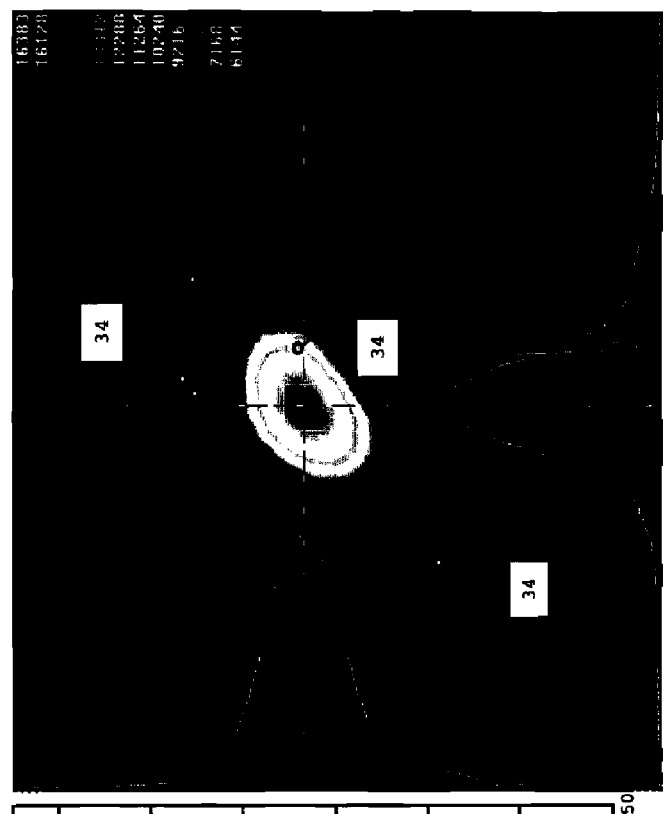
FIG. 8b reveals a projection of a flow channel image with particles.
Figure 8A:
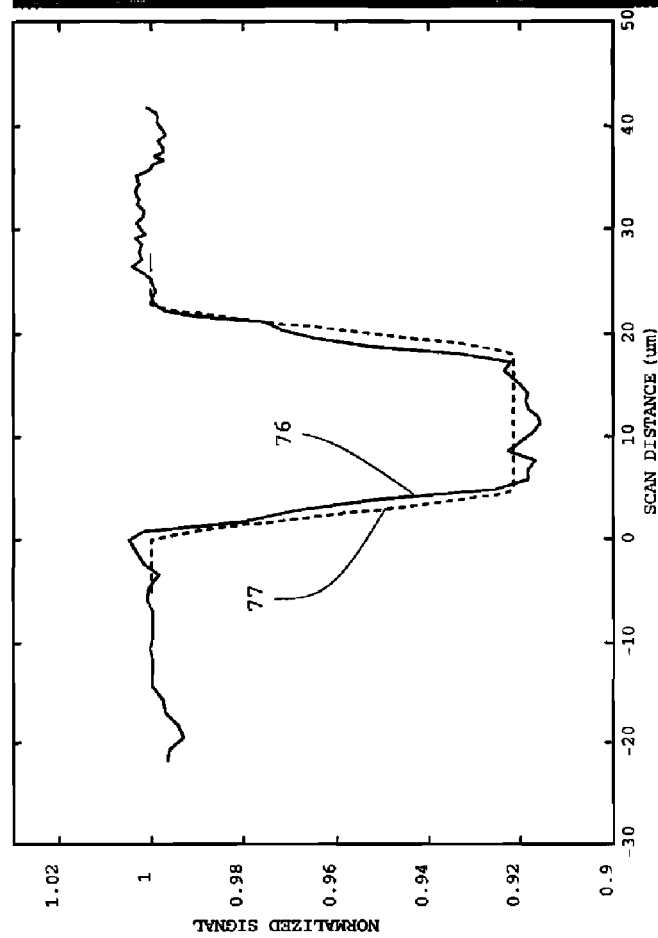
FIG. 8a shows static test results and model of beads in terms of a normalized signal versus a scan distance.

FIG. 8a shows static test-type results using 5 micron bead data in a system with a 676.7 nm laser and an f/50 focusing optic, as represented by a solid line 76 of the graph of the normalized signal versus scan distance. The signal to noise rating may be about 2224. The dashed line 77 is a fit to the measured profile using a model bead described in FIG. 4a. FIG. 8b shows a projection of an image 46 with particles 34 indicated.

An algorithm may be had for an optical determination of RBCs and PLTs. A sample 11 may be in put to the system 10, the sheath flow rates determined and the dilution factor calculated. An event may be detected where a threshold is exceeded in both pulses. The events may be segregated into simple and complex events. FIG. 3b shows an example of a simple event. FIG. 9a shows an example of a complex event. A complex event may involve an image 46 of a first particle or cell 34 crossing the first slit 47 and at least another image 46 of another particle or cell 34 crossing the first slit 47 before the image 46 of the first particle or cell 34 crosses the second slit 48. The first cell 34 crossing of slits 47 and 48 (in FIG. 3a) result in waveforms 51 and 52, respectively. The other particle 34 that crosses slit 47 before the first particle 34 crosses slit 48 may result in waveform 78, which appears before waveform 52 in FIG. 9a. The crossing of the other particle 34 may result in waveform 79. The distance 54 between waveforms 51 and 52 may be the same as the distance 54 between waveforms 78 and 79 because the flow rate is the same for the first and second particles 34. The amplitudes 57 and the pulse widths 56 for the waveforms 51, 52 and 78, 79 appear to be the same which means that the first and second particles may have about same diameter and size. It is likely that these particles are the same kind.

FIG. 9b also reveals a complex event. The image 48 of a first particle 34 may cross the first slit 47 and the image also may show a second particle 34 crossing the first slit 47 before the first particle 34 is shown to cross the second slit 48. This activity may be disclosed by waveforms from detector 41. Waveform 51 represents the first particle 34 of the image 46 crossing the first slit 47 and a waveform 81 represents the second particle 34 crossing the first slit 47. The waveform 52 may reveal the image of the first particle 34 crossing the second slit 48 and waveform 82 may reveal the second particle 34 of image 46 crossing the second slit 48.

The distance 54 between waveforms 51 and 52 appear to be the same as the distance 54 between the waveforms 81 and 82 since the flow rate may be about the same for the first and second particles 34. The amplitudes 57 of the pulse widths 56 of waveforms 51 and 81 appear different. The pulse applitude 57 and width 56 of the waveform 51 are noticeably larger than the pulse amplitude and width of waveform 81. That may indicate particles 34 of two different sizes. For example, if waveforms 51 and 52 represent RBCs, then waveforms 81 and 82 could represent platelets, particularly if the types of particles are known to be these. Thus, the particles 34 may be distinguishable from one another and data may be taken, and parameters measured and calculated, from detector 41 information to control electronics 23.

To reiterate, relative to the algorithm for the optical determination of RBCs and PLTs, the sample 11, sheath flow rates may be determined and the dilution factor calculated. A relevant event may be detected where a threshold is exceeded by both pulses. The events may be segregated into the simple and complex events. The single events may be processed first. The local flow velocity of the particles 34 may be measured and the pulse width in time may be measured. The pulse width in distance may be calculated, i.e., time divided by velocity. The pulse amplitude may be calculated from waveform signals from the detector 41. Amplitude versus diameter data may be generated and presented in the form of a table and/or graph. Then the PLT, multiple PLT, single RBC and multiple RBC events may be classified. An RBC parameter may be accumulated as 1*single RBC+2*dual RBC+3*triple RBC and . . . events. A PLT parameter may be accumulated as a 1*single PLT+2*dual PCT+3*triple PCT + . . . events.

Then, the complex events may be processed. Each complex event may be decomposed into simple events. Next, the simple event process, as noted herein, may be applied to the latter events. A dilution factor correction may be applied to the RBC and PLT parameters. Then the RBC and PLT parameters may be reported.

An optical determination may be made of the MCV and RDW with an algorithm described herein. An event that exceeds a threshold in both pulses may be detected. The local flow velocity and the pulse width in time may be measured. The pulse width in distance may be calculated with time divided by velocity. The pulse amplitude may be calculated. The amplitude versus the diameter may be generated for the events. The events may be checked and each identified single RBC be noted. If an event or events are identified as an RBC, then the pulse may be converted into a cell diameter. The formula used may be "Pulse width=C(cell diameter plus slit width)". The diameters may be accumulated and the cell diameters be converted to cell volumes. For such converting, the formula used may be "Cell volume=$(\pi/6)$ times (cell diameter)$^3$". Then one may calculate and report the MCV and RDW.

Figure 10B:
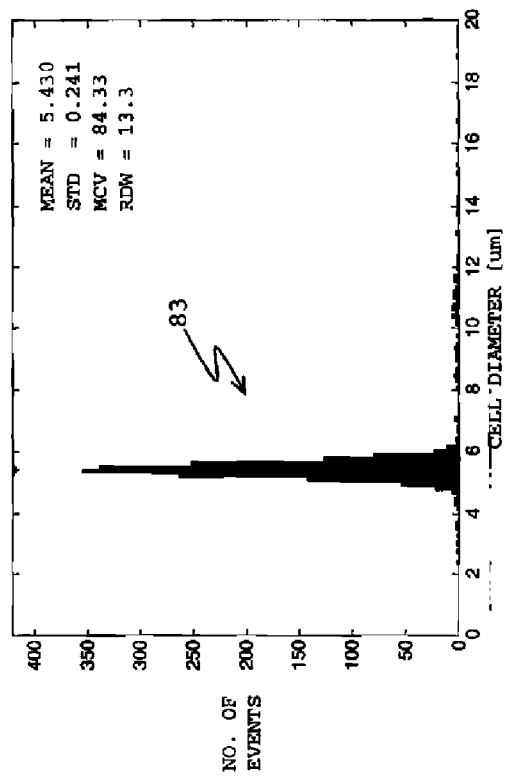
FIGS. 10b and 10c are histograms of measured pulse amplitude and pulse width (cell diameter)
Figure 10A:
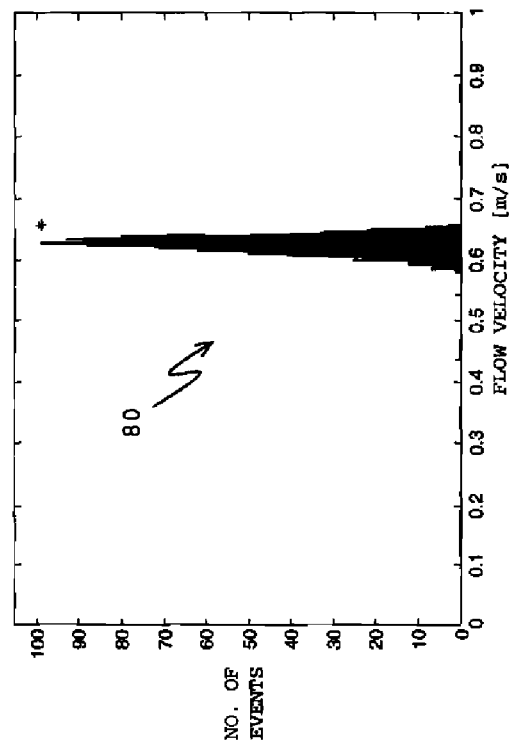
FIG. 10a is a histogram of the flow velocity.
Figure 10C:
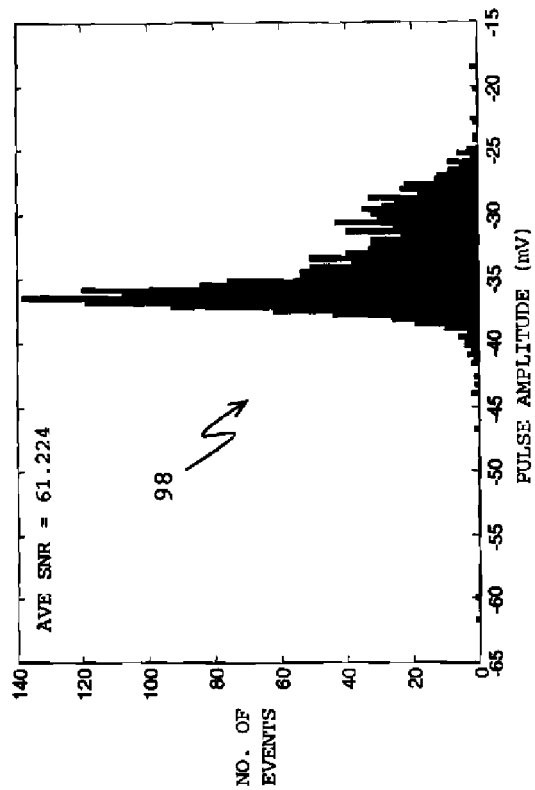
Figure 10D:
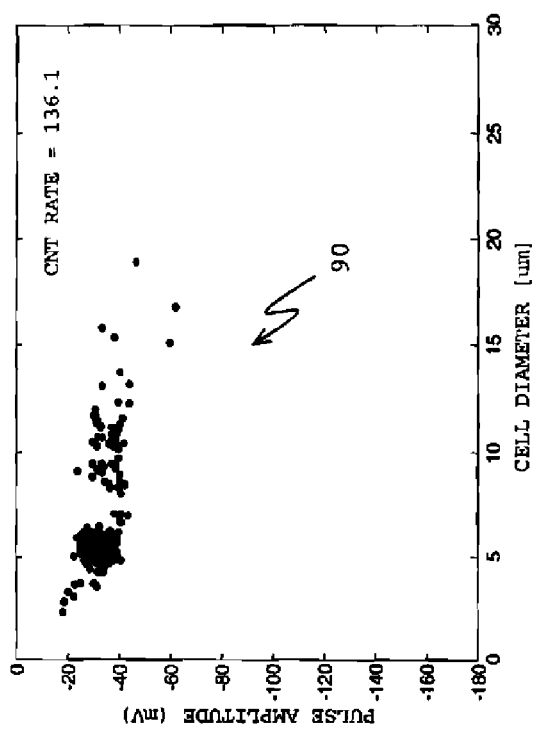
FIG. 10d is a scatter plot of pulse amplitude versus cell diameter for precision beads with diameter of 5.43 microns.

FIGS. 10a, 10b, 10c and 10d are measured plots 80, 83, 90 and 98, respectively, that reveal typical bead data for a laboratory test bed built to demonstrate this invention. FIG. 10a shows a distribution of the number of events versus the flow velocities in meter per second (m/s). FIG. 10b shows a distribution of the number events versus the cell diameters in microns. The resultant determinations from these data may reveal a mean diameter of 5.430 microns with a standard deviation of 0.241 micron, an MCV of 84.33, and an RDW of 13.3. FIG. 10c reveals pulse amplitudes in millivolts versus cell diameter in microns for a count rate of 136.1. FIG. 10d shows a distribution of a number of events versus the pulse amplitude in millivolts. The average SN ratio here appears to be 61.224.

Figure 11B:
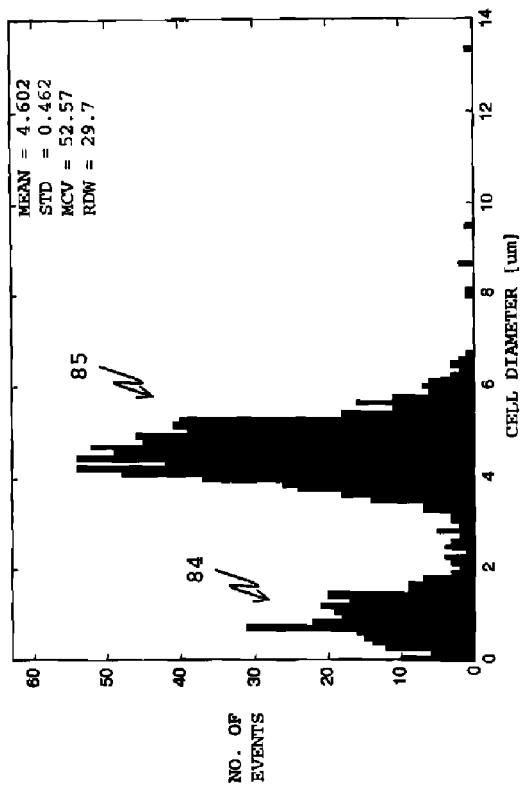
FIGS. 11a, 11b and 11c are histograms of measured flow velocity, cell diameter, and pulse amplitude, respectively.
Figure 11A:
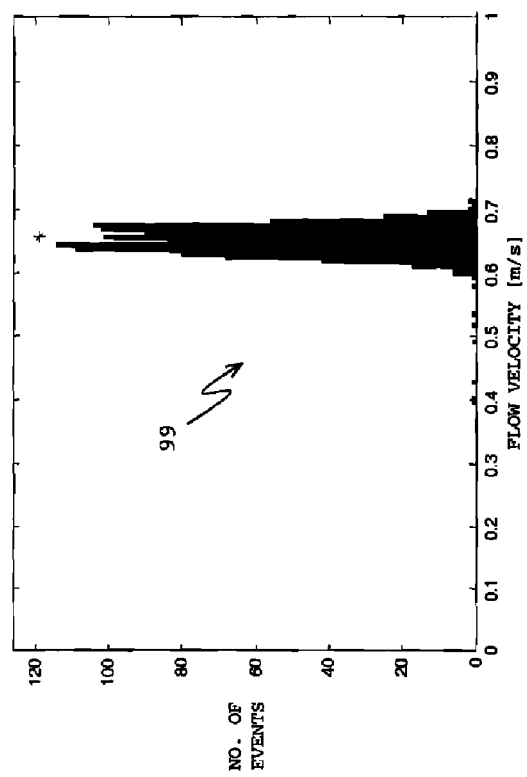
Figure 11D:
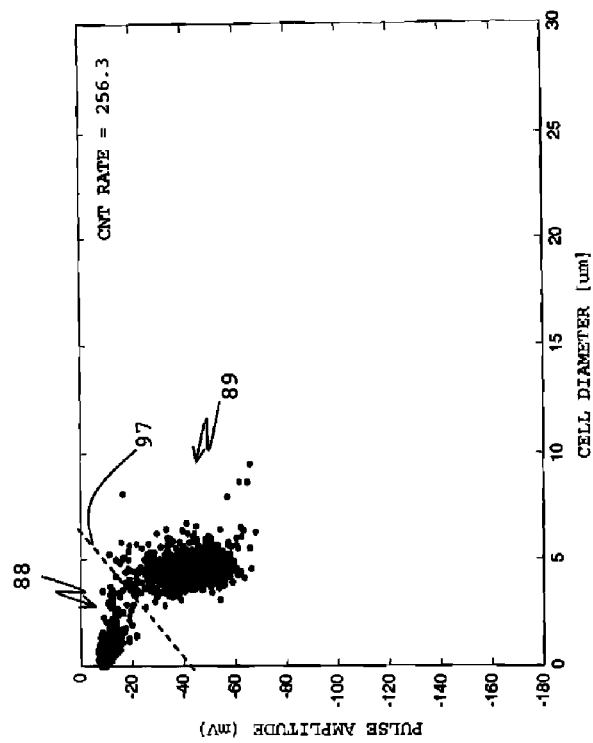
FIG. 11d is a scatter plot of pulse amplitude versus cell diameter for a mixture of a platelets and red blood cells.

FIGS. 11a, 11b, 11c and 11d are similar results involving testing and measurements of a PLT and RBC mixture. FIG. 11a shows a histogram 99 with a number of events versus a flow velocity in m/s. FIG. 11b shows a number of events versus cell diameter in microns. On may note a clump 84 of bars around one micron and a clump 85 of bars around 4.5 microns. These clumps 84 and 85 appear to represent the PLTs and RBCs, respectively. For the RBCs, there appears to be a mean diameter of 4.602 microns with a standard deviation of 0.462 micron, an MCV of 52.57 and an RDW of 29.7.

Figure 11C:
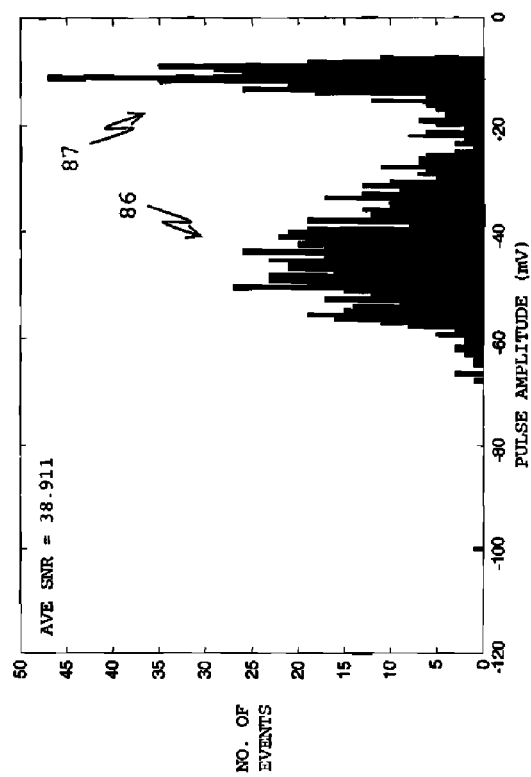

FIG. 11c shows a number of events versus pulse amplitude in millivolts. There appears to be a clump of bars 86 of centered about −45 millivolts and a clump of bars 87 centered about −12 millivolts. The average SN ratio appears to be about 38.911. The largest absolute value which is clump 86 appears to represent RBCs and the other clump 87 appears to represent PLTs. Clumps 84 and 86, and clumps 85 and 87 seem to corroborate each other. Such corroboration may be illustrated in FIG. 11d where the pulse amplitude for the events is plotted with the cell diameters from FIGS. 11b and 11c, respectively. This plotting appears to result in two groupings 88 and 89 which correspond to the PLTs and RBCs. The count rate here may be about 256.3. One may note a division between clumps 84 and 85 at about 2.5 microns, and between clumps 86 and 87 at about 22 millivolts. One may use these values as a coordinate in FIG. 11d and draw a line 97 through that coordinate at about 45 degrees to show an approximate dividing line between the PLTs of group 88 and the RBCs of group 89.

Figure 12B:
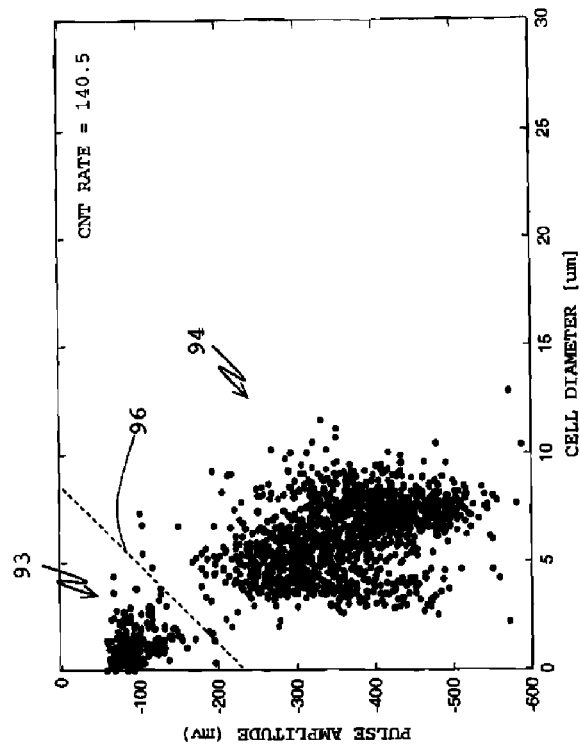
FIGS. 12a and 12b are scatter plots of pulse amplitude versus cell diameter that reveal several types of cells in a sample.
Figure 12A:
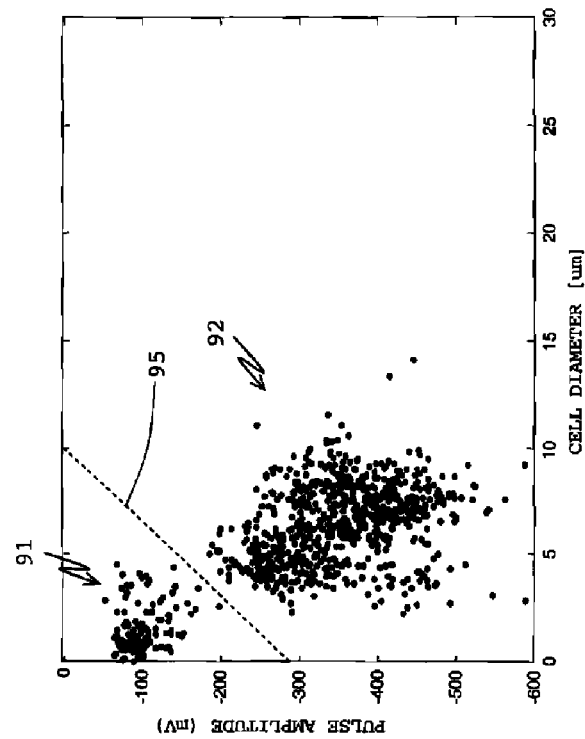

FIGS. 12a and 12b provide corroboration for the optical distinguishing of the particle types (i.e., RBCs and PLTs) in a blood sample. The experiment dealt with pre-sphered blood as the type of sample. From these plots, one can see the two groups 91 and 92 in FIG. 12a, and groups 93 and 94 in FIG. 12b, represent the PLTs and RBCs, respectively. Lines 95 and 96 may divide the two groups 91 and 92, and groups 93 and 94 respectively, in the same manner as line 97 relative to groups 88 and 89 in FIG. 11d.

In the present specification, some of the matter may be of a hypothetical or prophetic nature although stated in another manner or tense.

Although the invention has been described with respect to at least one illustrative example, many variations and modifications will become apparent to those skilled in the art upon reading the present specification. It is therefore the intention that the appended claims be interpreted as broadly as possible in view of the prior art to include all such variations and modifications.

What is claimed is:

1. A particle analysis system comprising:
a channel;
a hydrodynamic focusing module connected to the channel;

a projection system proximate to the channel;
a screen having a slit aperture proximate to the channel; and
a dual sensor detector proximate to the slit aperture; and
wherein the slit aperture comprises a first slit and a second slit; and
signals from the first slit and the second slit provide information about speeds of the particles;
wherein a width of the signal provides information about a diameter of the particle; an amplitude of the signal provides information for discriminating different kinds of particles; and/or the amplitude of the signal provides counts of the particles; the width of the signal provides information for discriminating different kinds of particles; the width of the signal provides counts of the particles; a combination of width and amplitude of the signal provides information for discriminating different kinds of particles; and the combination of width and amplitude of the signal provides counts of particles.

2. The system of claim 1, wherein the channel and the hydrodynamic focusing module are situated in a cartridge.

3. The system of claim 1, wherein:
the channel is for conveying particles;
the projection mechanism is for displaying an image of the particles in the channel on the screen; and
the detector is for detecting a portion of the image through the slit aperture; and
wherein the detector, upon detecting an image of a particle through the slit aperture, outputs a signal.

4. The system of claim 3, wherein the particles are blood cells.

5. The system of claim 1, wherein:
the particles are red blood cells and platelets;
the counts comprise a count of red blood cells and a count of platelets;
diameters of the red blood cells of the count of the red blood cells are approximately determined;
a mean cell volume of the count of the red blood cells is approximately determined;
a red cell distribution width of the count of red blood cells is approximately determined; and/or
a hematocrit is approximately determined from a product of the count of the red blood cells and the red cell distribution width.

6. The system of claim 1, further comprising;
a hemoglobin module for approximately determining an amount of hemoglobin in a blood sample; and
wherein:
a mean cell hemoglobin is approximately determined by the amount of hemoglobin divided by the count of the red blood cells; and/or
a mean cell hemoglobin concentration is approximately determined by the count of the red blood cells divided by the hematocrit.

7. A method for determining particle parameters comprising:
measuring a flow rate with a flow rate sensor;
hydrodynamically focusing particles of a fluid sample into a single file through a flow channel;
projecting a light through the flow channel;
focusing an image of the particles in the flow channel onto a multiple slit aperture;
detecting obscurations of light from the aperture;
converting the obscurations of light into waveforms representative of the obscurations of light; and
processing the waveforms into data about the particles;
calculating a particle diameter from a product of the calibration factor and the pulse width in distance, and minus the slit width from the product.

8. The method of claim 7, wherein the data from the detecting comprises:
flow rate;
measurement time;
count of particles;
pulse width in time;
pulse amplitude; and/or
particle transit time.

9. The method of claim 8, further comprising doing an analysis of the particles to attain a number of first type particles and a number of second type particles in the fluid sample by means of one or more of the following operations:
a histogram of measured particle pulsewidths; or
a histogram of measured particle amplitudes; or
a combined scatter plot of measured particle pulsewidths versus measured particle amplitudes.

10. The method of claim 9, wherein:
the fluid sample is a blood sample;
the first type particle is a red blood cell; and
the second type particle is a platelet.

11. The method of claim 8, further comprising:
calculating a first type particle count per volume from a number of first type particles counted divided by a product of a dilution factor, a flow rate and a measurement time; and
calculating a second type particle count per volume from a number of second type particles counted divided by a product of the dilution factor, the flow rate and the measurement time.

12. The method of claim 7, further comprising:
measuring slit pitch of the multiple slit aperture; and/or
measuring slit width.

13. The method of claim 12, further comprising:
calculating a flow velocity of the particles from slit pitch divided by particle transit time; and/or
calculating a pulse width in distance from a product of flow velocity and pulse width in time.

14. The method of claim 13, further comprising determining a calibration factor.

15. The method of claim 7, further comprising:
obtaining a particle flow rate; and
determining a dilution factor of the fluid sample.

16. The method of claim 7, further comprising:
calculating a mean particle volume (MCV) from a product of a cube of an average first type particle diameter and $\pi/6$; and
calculating a first type particle distribution width (RDW) from a product of standard deviation and a first type particle diameter and $\pi/6$, divided by the MCV.

17. The method of claim 16, further comprising calculating a hematocrit (Hct) from a product of a first type particle count per volume and an MCV.

18. The method of claim 17, further comprising:
measuring an amount of hemoglobin per unit volume (Hb) of the fluid sample;
calculating a mean cell hemoglobin concentration (MCHC) from the Hb divided by the Hct; and
calculating a mean cell hemoglobin (MCH) as a product of the MCHC and the MCV.

* * * * *